United States Patent [19]

Kabbe et al.

[11] Patent Number: 4,510,156
[45] Date of Patent: Apr. 9, 1985

[54] BISINDOLYL ALKYLENE UREAS LIPID ABSORPTION-INHIBITING AGENTS AND THEIR USE THEREAS

[75] Inventors: Hans-Joachim Kabbe, Leverkusen; Hans-Peter Krause; Rüdiger Sitt, both of Wuppertal, all of Fed. Rep. of Germany

[73] Assignee: Bayer Aktiengesellschaft, Leverkusen, Fed. Rep. of Germany

[21] Appl. No.: 347,599

[22] Filed: Feb. 10, 1982

Related U.S. Application Data

[62] Division of Ser. No. 206,314, Oct. 31, 1980, abandoned.

[30] Foreign Application Priority Data

Nov. 9, 1979 [DE] Fed. Rep. of Germany ....... 2945238
Aug. 8, 1980 [DE] Fed. Rep. of Germany ....... 3030024

[51] Int. Cl.³ .................... A61K 31/40; C07D 403/12; C07D 209/26
[52] U.S. Cl. .................... 514/415; 548/492; 548/455
[58] Field of Search ................. 548/492, 455; 424/274

Primary Examiner—Glennon H. Hollrah
Assistant Examiner—D. B. Springer
Attorney, Agent, or Firm—Sprung, Horn, Kramer & Woods

[57] ABSTRACT

The invention relates to alkylurea derivatives of Formula (I), as defined in the specification, which alkylurea derivatives are useful as hypolipaemic agents. Also included in the invention are methods for the manufacture of said alkylurea derivatives compositions and medicaments containing said alkylurea derivatives and methods for the use of said alkylurea derivatives.

15 Claims, No Drawings

BISINDOLYL ALKYLENE UREAS LIPID ABSORPTION-INHIBITING AGENTS AND THEIR USE THEREAS

This is a division, of application Ser. No. 206,314, filed Oct. 31, 1980, abandoned.

The present invention relates to the use of, as agents for influencing the lipometabolism, certain alkylurea compounds some of which are known.

Alkylurea derivatives, used according to the invention, which are already known are disclosed in M. Mazza et al, Farmaco, Ed. Sci. 32, No. 1, 54–66 (1977). Phytotoxic effects have already been described for these known compounds. Some derivatives of ethoxyquin can also be used as inhibitors of iron poisoning (see DT-OS (German Published Specification) No. 2,802,630). Their effect on the lipometabolism, and in particular their lipid absorption-inhibiting effect, has not yet been disclosed hitherto.

According to the present invention there is provided a pharmaceutic composition containing as an active ingredient, a compound which is an alkylurea of the formula $$\text{(I)}$$

in which
Y represents R or a radical $$-(CH_2)_{n1}-(X)_l-(CH_2)_{n2}-NH-C=X$$

in which
$n_1$ and $n_2$ denote integers from 3 to 9 and $l$ denotes 0 or 1 and in which
R represents a straight-chain, branched, cyclic, saturated or unsaturated aliphatic hydrocarbon radical with up to 20 carbon atoms, which is optionally substituted by halogen, hydroxyl, alkoxy, alkoxy-carbonyl, or optionally substituted aryl, $R^1$ represents a hydrogen atom or a $C_1$-$C_6$ alkyl radical, $R^2$ represents a $C_1$-$C_6$ alkyl radical and $R^3$, and $R^4$ and $R^5$ are identical or different and each represent a hydrogen or halogen atom or a hydroxyl, cyano, $C_1$-$C_6$ alkyl, $C_1$-$C_6$ alkoxy, ($C_1$-$C_6$ alkoxy)-carbonyl, $C_1$-$C_6$ alkylmercapto, $C_1$-$C_6$ alkylsulphonyl, $C_1$-$C_6$ alkylsulphinyl, ($C_1$-$C_6$ alkyl)-carbonyl, optionally substituted aryl or optionally substituted aryloxy radical, X denotes oxygen or sulphur and
A represents one of the following radicals $$-\underset{R''}{\overset{R'}{C}}-, \quad -\underset{R''}{\overset{R'}{C}}-CH_2-, \quad -\underset{}{\overset{R'}{C}}=CH-, \quad -O-\underset{R''}{\overset{R'}{C}}-,$$

$$-N-\underset{R''}{\overset{R'''}{\underset{|}{C}}}-, \quad -S(O)_m-\underset{R''}{\overset{R'}{C}}-$$

in which
R' and R'' are identical or different and each denote a hydrogen atom or a $C_1$-$C_6$ alkyl radical,
R''' denotes a $C_1$-$C_6$ alkyl radical and
m is 0, 1 or 2, in admixture with a solid or liquefied gaseous diluent or in admixture with a diluent other than a solvent of molecular weight less than 200 except in the presence of a surface active agent.

Surprisingly, the alkylurea derivatives of the formula (I) display a powerful lipid adsorption-inhibiting action. Knowing the prior art, it could not be expected that compounds of this category of substances can be used as lipid absorption-inhibiting active substances.

The use of the compounds according to the invention for the first time in the control of hyperlipaemia makes it possible also to treat those patients who display intolerance or habituation towards the lipid absorption-inhibitors which are already known. These compounds thus represent an enrichment of pharmacy.

According to the present invention, there are further provided processes for the production of compounds used according to the invention in which:

(a) an amine of the formula $$\text{(II)}$$

in which A and $R^1$ to $R^5$ have the abovementioned meaning, is reacted with a compound of the formula $$R-N=C=X \qquad \text{(III)}$$

in which R and X have the abovementioned meaning, or with a compound of the formula $$X=C=N-(CH_2)_{n1}-(X)_l-(CH_2)_{n2}-N=C=X \qquad \text{(IV)}$$

in which X, $n_1$, $n_2$, and $l$ have the abovementioned meaning optionally in an inert organic solvent and optionally in the presence of a catalyst for isocyanate reactions, at a temperature between 20° and 120° C., or (b) an amine of the formula (II) is reacted with phenyl chloroformate of the formula $$ClCOOC_6H_5 \qquad \text{(V)}$$

at a temperature between 0° and 50° C., and the resulting phenylcarbamic acid ester of the formula

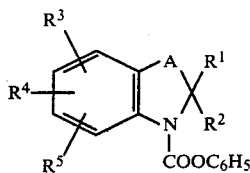 (VI)

in which A and $R^1$ to $R^5$ possess the abovementioned meaning,
is reacted directly or after it has been isolated, with an amine of the formula $$H_2N-R \quad (VII)$$

or with a diamine of the formula (VIII)

$$H_2N-(CH_2)_{n1}-(X)_l-(CH_2)_{n2}-NH_2 \quad (VIII)$$

in which R, $n_1$, $n_2$ and l have the abovementioned meanings, in an inert organic solvent at a temperature between 20° and 140° C.

Reaction variant (b) yields alkylurea derivatives in which X denotes oxygen.

Particularly preferred compositions according to the present invention are those containing as active ingredient a compound which is an alkylurea of the formula (I) in which R represents a straight-chain, branched, cyclic, saturated or unsaturated aliphatic hydrocarbon radical with 4 to 20 carbon atoms, which is optionally substituted by halogen (preferably chlorine, bromine or fluorine), trifluoromethyl, hydroxyl or alkoxy or alkoxycarbonyl, with, in each case, 1 to 6 carbon atoms in the alkoxy radical, or by phenyl, the phenyl radical in turn optionally carrying 1 or 2 substituents selected from halogen, trifluoromethyl, hydroxyl, alkyl with 1 to 2 carbon atoms and alkoxy with 1 to 2 carbon atoms.

$R^1$ represents a hydrogen atom or an alkyl radical with 1 to 4 carbon atoms, $R^2$ represents an alkyl radical with 1 to 4 carbon atoms, $R^3$, $R^4$ and $R^5$ are identical or different and each represent a hydrogen or halogen (preferably chlorine, bromine or fluorine) atom or a hydroxyl, cyano, trifluoromethyl, alkyl, alkylmercapto, alkylsulphonyl, alkylsulphinyl, alkylcarbonyl, alkoxy or alkoxycarbonyl radical, the abovementioned alkyl and alkoxy radicals and moieties containing 1 to 4 carbon atoms in each case, or represent a phenyl or phenoxy radical, the phenyl radical or moiety optionally being monosubstituted or disubstituted by halogen trifluoromethyl or alkoxy with 1 to 2 carbon atoms, X denotes oxygen or sulphur and
A represents one of the following radicals:

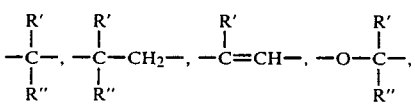

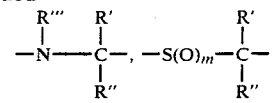

in which
R' and R" are identical or different and each denote a hydrogen atom or an alkyl radical with 1 to 4 carbon atoms,
R'" denotes an alkyl radical with 1 to 4 carbon atoms and m is 0 or 2.

According to the present invention we further provide novel alkylureas of the formula (I) in which:

R represents straight-chain, branched or cyclic alkyl or alkenyl with 6 to 18 carbon atoms, the said alkyl and alkenyl groups optionally being substituted by chlorine, bromine, fluorine or alkoxy with 1 to 4 carbon atoms, or by phenyl, $R^1$ and $R^2$ are identical or different and each represent alkyl with 1 or 2 carbon atoms, $R^3$, $R^4$ and $R^5$ are identical or different and each represent hydrogen, chlorine, bromine, trifluoromethyl, alkyl, alkylmercapto or alkoxy, the said alkyl and alkoxy radicals each containing 1 to 4 carbon atoms, or represent phenoxy or chlorophenoxy, A represents one of the following radicals:

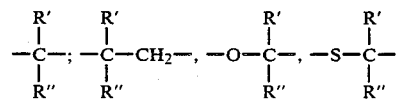

in which
R' and R" are identical or different and each denote hydrogen, methyl or ethyl, and X represents oxygen.

Particularly preferred novel alkylurea of the formula (I) are those in which

R denotes straight-chain, branched or cyclic alkyl or alkenyl with, in each case, 6 to 18 carbon atoms, optionally substituted by chlorine, bromine, fluorine or alkoxy with 1 to 4 carbon atoms, $R^1$ and $R^2$ denote methyl or ethyl, $R^3$, $R^4$ and $R^5$ denote hydrogen, chlorine, bromine, trifluoromethyl, phenoxy, chlorophenoxy or alkyl mercaptoalkyl or alkoxy with, in each case, 1 to 2 carbon atoms, X denotes oxygen and
A represents one of the following radicals:

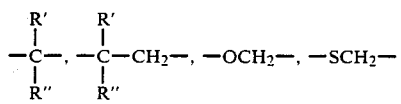

in which
R' and R" in each case represent a hydrogen atom or a methyl or ethyl group.

Further the new alkylurea derivatives of the formula (I) which are also of particular interest are those in which:
Y represents a radical

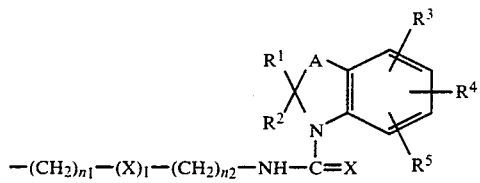

$$-(CH_2)_{n1}-(X)_l-(CH_2)_{n2}-NH-\overset{|}{C}=X$$

in which
$R^1$, $R^2$, $R^3$, $R^4$, $R^5$, X, A, $n_1$, $n_2$, and l correspond to the above definitions.

Examples of new compounds which may be mentioned are: N-n-hexylaminocarbonyl-2,2,4-trimethyl-1,2,3,4-tetrahydroquinoline, N-n-octylaminocarbonyl-2,2,4-trimethyl-1,2,3,4-tetrahydroquinoline, N-2-ethylhexylaminocarbonyl-2,2,4-trimethyl-1,2,3,4-tetrahydroquinoline, N-n-tetradecylaminocarbonyl-2,2,4-trimethyl-1,2,3,4-tetrahydroquinoline, N-3-n-butoxypropylaminocarbonyl-2,2,4-trimethyl-1,2,3,4-tetrahydroquinoline, N-n-hexylaminocarbonyl-2-methylindoline, N-n-hexylaminocarbonyl-2,2-dimethylindoline, N-n-dodecylaminocarbonyl-2,2-dimethylindoline, N-n-octylaminocarbonyl-2,2,4-trimethyl-6-phenoxy-1,2,3,4-tetrahydroquinoline and N-n-octylaminocarbonyl-2,2,4-trimethyl-6-butoxy-1,2,3,4-tetrahydroquinoline, 6,6'-bis-(N-2,2,4-trimethyl-1,2,3,4-tetrahydroquinolyl)-di-n-hexyl ether and 6,6'-bis-(N-2,2,4-trimethyl-1,2,3,4-tetrahydroquinolyl)-di-n-butyl ether.

The novel compounds of the present invention may be prepared by the above-mentioned process variants (a) and (b) using appropriate starting materials.

The isocyanate derivatives, amines and phenylcarbamic acid esters of the formulae (III), (IV), (VI) (VII) and (VIII) which are used as starting materials in the processes according to the present invention, are known compounds or can be prepared by known methods [see R. Wagner et al, Synthetic Organic Chemistry, Wiley, New York, (1953), pages 640, 645 and 653, and Beilstein, Volume XX, 2nd supplementary volume, pages 180, 192 and 210].

The compounds of the formula (I) display an advantageous inhibition of lipid absorption in warm-blooded animals. When fat-containing food is taken in, the compounds of the formula (I) result in a lower alimentary hyperlipaemia, coupled with simultaneous inhibition of cholestrol adsorption, so that they can be used in particular for the treatment of lipometabolism disorders, such as hyperlipoproteinaemia, arteriosclerosis or adiposity.

The advantageous effect can be demonstrated on rats using the following test arrangement:

2.5 ml/kg of olive oil are administered per os to one group of rats (control group) in order to produce an alimentary hyperlipaemia. A corresponding group of other rats receives the active substance in the form of a suspension in gum tragacanth, administered by probang, at the same time as the olive oil is administered. Gum tragacanth only is administered to a further control group of rats.

2 hours after the administration of olive oil, the concentrations of the serum triglycerides are determined in all three groups of rats (method: J. Ziegenhorst, Kiln. Chem. 21, (1975) 1,627). Two hours after the administration of fat, the rats treated with olive oil only (group 1) show a distinct rise in the serum triglycerides, compared with the rats to which no fat was administered (group 3). The lesser rises in the serum triglycerides levels in the animals treated with active substance and olive oil (group 2) are compared with this rise, which is taken as 100%. It is found that even low dosages of the urea derivatives of the formula (I) cause a significant lowering in the serum triglycerides levels. In addition to the powerful lipid absorption-inhibiting action, the compounds also display an outstandingly good tolerance.

As stated above, the invention also relates to the use in medicine of the compounds of the invention.

The present invention provides pharmaceutical compositions containing as active ingredient a compound of the invention in admixture with an inert pharmaceutical carrier, such as a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physcially discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents or syrups.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine, and polyvinyl pyrrolidone; (c) moisturizing agents, e.g. glycerol; (d) distintegrating agents, e.g. agar-agar, calcium carbonate and sodium bicarbonates; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents i.e. inert pharmaceutical carriers (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as lipid diluents, e.g. water, ethyl alcohol, propylene glycol, surface-active agents (e.g. ethoxylated isostearyl alcohols, polyoxyethylene sorbite and sorbitane esters), micrycrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95%, of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents or molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 50 to 2,500 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably locally. Preferred pharmaceutical compositions and medicaments are therefore those adapted for administration such as oral administration. Administration in the method of the invention is preferably oral administration.

In general it has proved advantageous to administer amounts of from 0.1 mg to 100 mg/kg, preferably from 1 mg to 50 mg/kg, of body weight per day, divided into 1 to 6 administrations, to achieve effective results. An individual administration preferably contains the active compound or compounds in amounts of 0.1 to 20 mg/kg of body weight. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The formulation examples which follow illustrate the preparation of medicinal formulations to be used according to the invention:

Examples of the preparation of tablets 1. 100 mg of the compound of Example 1 are mixed with 69 mg of lactose and 30 mg of maize starch, the mixture is then kneaded with a paste of 15 mg of maize starch and the whole is pressed through a sieve of 3-5 mm mesh width. The mixture is then dried in a drier at 60°-80° C.

The resulting granules are forced through a sieve of 0.8 mm mesh width, a further 15 mg of maize starch, 10 mg of talcum and 1 mg of magnesium stearate are mixed in and the resulting mixture is compressed with the aid of a conventional tablet press to give round tablets with a diameter of 9 mm and total weight of 240 mg.

2. 200 mg of the compound of Example 13 are mixed with 97 mg of secondary calcium phosphate and the mixture is kneaded with an aqueous gelatine solution which contains 2 mg of gelatine. The resulting mixture is then pressed through a sieve of 3-5 mm mesh width and dried at 60°-80° C. The dry granules are sieved (0.8 mm), 20 mg of wheat starch and 1 mg of magnesium stearate are then mixed in and the resulting mixture is tabletted in the known manner. Round tablets with a diameter of 8 mm and a total weight of 320 mg are obtained.

The following Examples illustrate processes for the production of alkylurea compounds used according to the present invention.

EXAMPLE 1

(variant a)

0.1 mole of 2,2,4-trimethyl-1,2,3,4-tetrahydroquinoline is dissolved in 50 ml of ether and the solution is mixed with 0.1 mole of n-dodecyl isocyanate. A spatula tip of diazadicyclooctane is then added, the mixture is left to stand for 7 days at 20° to 25° C. and cooled at −70° C. and the precipitate which has separated out is filtered off. N-n-Dodecylaminocarbonyl-2,2,4-trimethyl-1,2,3,4-tetrahydroquinoline with a melting point of 48°–50° C. is obtained.

Yield: 66% of theory.

EXAMPLE 2

(variant b)

1 mole of 2-methylindoline is dissolved in 300 ml of toluene and 1 mole of methyl isocyanate is added, the temperature not rising above 25° C. The mixture is left to stand for 1 day and the resulting precipitate is then filtered off. N-Methylaminocarbonyl-2-methylindoline with a melting point of 158°–160° C. is obtained.

Yield: 89% of theory.

EXAMPLE 3

(variant b)

A solution of 0.1 mole of 2-methylindoline, 0.12 mole of triethylamine, 100 ml of toluene and 0.1 mole of phenyl chloroformate is kept at 40° C. for 10 hours and is then cooled to 20° C. and stirred with 250 ml of water for 15 minutes. The toluene phase is separated off, the solvent is evaporated in vacuo, the residue is dissolved in 100 ml of n-hexylamine and this solution is heated under reflux at 130° C. for 6 hours. After cooling, the solvent is evaporated off at 50° C./10 mm Hg and the residue is taken up in 250 ml of toluene. The solution is then extracted successively with 200 ml of 1N sodium hydroxide solution, 200 ml of 1N hydrochloric acid and 200 ml of water. After concentrating the solution, the residue is recrystallised from petroleum ether. N-n-Hexyl-aminocarbonyl-2-methylindoline with a melting point of 57°–59° C. is obtained.

Yield: 53% of theory.

The compounds in the table which follows are obtained analogously to Example 1.

TABLE

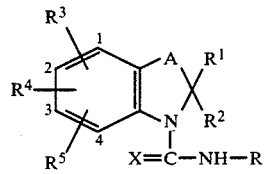

| Example No. | A | X | R | $R^1$ | $R^2$ | $R^3, R^4, R^5$ | Melting point (°C.) | Yield in % of theory | Remarks |
|---|---|---|---|---|---|---|---|---|---|
| 4 | —S—CH$_2$— | O | n-C$_{12}$H$_{25}$ | CH$_3$ | CH$_3$ | H | 102–104 | 24 | |
| 5 | —C=CH—<br>\|<br>CH$_3$ | O | n-C$_{12}$H$_{25}$ | CH$_3$ | CH$_3$ | H | 70–71 | 36 | |
| 6 | —C=CH—<br>\|<br>CH$_3$ | O | n-C$_{12}$H$_{25}$ | CH$_3$ | CH$_3$ | 2-Cl | | 94 | oil |
| 7 | —C=CH—<br>\|<br>CH$_3$ | O | n-C$_{12}$H$_{25}$ | CH$_3$ | CH$_3$ | 2-OC$_2$H$_5$ | 56–57 | 71 | |
| 8 | —CH—CH$_2$—<br>\|<br>CH$_3$ | O | n-C$_{12}$H$_{25}$ | CH$_3$ | CH$_3$ | 2-OC$_2$H$_5$ | | 98 | oil |
| 9 | —CH—CH$_2$—<br>\|<br>CH$_3$ | O | n-C$_{16}$H$_{33}$ | CH$_3$ | CH$_3$ | H | 62–63 | 41 | |
| 10 | —CH—CH$_2$—<br>\|<br>CH$_3$ | O | n-C$_{18}$H$_{27}$ | CH$_3$ | CH$_3$ | H | 62–64 | 35 | |
| 11 | —CH—CH$_2$—<br>\|<br>CH$_3$ | O | CH$_3$ | CH$_3$ | CH$_3$ | H | 105–107 | 77 | |
| 12 | —CH—CH$_2$—<br>\|<br>CH$_3$ | O | iso-C$_3$H$_7$ | CH$_3$ | CH$_3$ | H | 79–81 | 31 | |

TABLE-continued

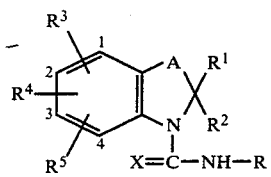

| Example No. | A | X | R | R¹ | R² | R³, R⁴, R⁵ | Melting point (°C.) | Yield in % of theory | Remarks |
|---|---|---|---|---|---|---|---|---|---|
| 13 | —CH—CH₂—<br>   \|<br>  CH₃ | O | (CH₂)₆—Cl | CH₃ | CH₃ | H | 71-73 | 68 | |
| 14 | —CH—CH₂—<br>   \|<br>  CH₃ | O | n-C₄H₉ | CH₃ | CH₃ | H | 48-50 | 54 | |
| 15 | —CH—CH₂—<br>   \|<br>  CH₃ | O | i-C₄H₉ | CH₃ | CH₃ | H | 68-70 | 42 | |
| 16 | —CH₂— | O | iso-C₃H₇ | H | CH₃ | H | 129-131 | 92 | |
| 17 | —CH₂— | O | n-C₄H₉ | H | CH₃ | H | 99-101 | 73 | |
| 18 | —CH₂— | O | tert.-C₄H₉ | H | CH₃ | H | 133-135 | 76 | |
| 19 | —CH₂— | O | (CH₂)₆—Cl | H | CH₃ | H | 74-76 | 89 | |
| 20 | —CH₂— | O | n-C₁₂H₂₅ | H | CH₃ | H | 78-80 | 91 | |
| 21 | —CH₂— | S | Allyl | H | CH₃ | H | | 98 | oil |

EXAMPLE 22

16.8 g of hexamethylene diisocyanate are added to a solution of 35 g of 2,2,4-trimethyl-1,2,3,4-tetrahydroquinoline in 100 ml of ether. After 1 day ½ g of DABCO (diazabicyclooctane) is added, the mixture is left to stand for 3 days and 23.8 g of 1,6-bis-(N-2,2,4-trimethyl-1,2,3,4-tetrahydroquinolyl)-carbonylaminohexane are filtered off. A further 25.1 g are obtained from the mother liquor (total yield: 48.1 g =94%).
Melting point: 125° to 128° C.

EXAMPLE 23

18.2 g of 1,7-diisocyanatoheptane are added to a solution of 35 g of 2,2,4-trimethyl-1,2,3,4-tetrahydroquinoline in 100 ml of absolute tetrahydrofurane. After 1 day, ½ g of DABCO is added. After standing for some time, a litter undissolved matter is filtered off, the filtrate is concentrated, the residue is dissolved in about 100 ml of ether, the solution is diluted with 200 mm of petroleum ether and cooled down to −70° C., and the precipitate is filtered off after 1 day. Yield of 1,7-bis-(N-2,2,4-trimethyl-1,2,3,4-tetrahydroquinolyl)-carbonylaminoheptane: 42.9 g; melting point 112° to 116° C.

EXAMPLE 24

A solution of 35 g of 2,2,4-trimethyl-1,2,3,4-tetrahydroquinoline, 23.8 g of 1.11-diisocyanatoundecane and ½ g of DABCO is left to stand for 3 days, 150 ml of toluene/petroleum ether (1:1) are added, the whole is briefly heated to the boil and the precipitate is filtered off. Yield: 46.4 g (83%) of 1,11-bis-(N-2,2,4-trimethyl-1,2,3,4-tetrahydroquinolyl)-carbonylamino-undecane. Melting point 102° to 108° C.

The further products are prepared analogously to Example 22, 23, or 24 (see Table 2 which follows), wherein the products of the process are defined in accordance with the formula

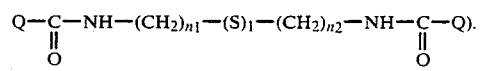

TABLE 2

| Example | Q | n₁ | n₂ | l | Yield (% of theory) | Procedure analogous to Example | Melting point (°C.) |
|---|---|---|---|---|---|---|---|
| 25 | ![structure with CH₃, CH₃, CH₃, N] | 4 | 4 | 0 | 48 | 23 | 93-98 |
| 26 | " | 6 | 6 | 1 | 42 | 24 | 78-79 |

TABLE 2-continued

| Example | Q | $n_1$ | $n_2$ | l | Yield (% of theory) | Procedure analogous to Example | Melting point (°C.) |
|---|---|---|---|---|---|---|---|
| 27 | (2-methylindoline) | 6 | 5 | 0 | 80 | 23 | 66–68 |
| 28 | " | 3 | 3 | 0 | 95 | 23 | 158–60 |
| 29 | (6-isopropoxy-2,2,4-trimethyl-1,2,3,4-tetrahydroquinoline) | 6 | 5 | 0 | 39 | 22 | 64–68 |
| 30 | (6-methoxy-2,2,4-trimethyl-1,2,3,4-tetrahydroquinoline) | 6 | 5 | 0 | 52 | 22 | 81–84 |

The compounds in Table 3 which follows are obtained analogously to Example 1, A, X, R, $R^1$, $R^2$ and $R^3$ being defined in accordance with Table 1.

TABLE 3

| Example No. | A | X | R | $R^1$ | $R^2$ | $R^3$, $R^4$, $R^5$ | Melting point (°C.) | Yield in % of theory |
|---|---|---|---|---|---|---|---|---|
| 31 | $-CH(CH_3)-CH_2-$ | O | $CH_2-CF_3$ | $CH_3$ | $CH_3$ | H | 120–122 | 86 |
| 32 | $-CH_2-CH_2-$ | O | $C-C_6H_{11}$ | $CH_3$ | H | H | 57–59 | 66 |
| 33 | $-CH_2-CH_2-$ | O | $n-C_{12}H_{25}$ | $CH_3$ | H | H | 44–46 | 74 |
| 34 | $-CH_2-CH_2-$ | O | $CH_3$ | $CH_3$ | H | H | 70–72 | 82 |
| 35 | $-C(CH_3)=CH-$ | O | $C-C_6H_{11}$ | $CH_3$ | $CH_3$ | $2-OC_2H_5$ | 135–137 | 79 |
| 36 | $-CH(CH_3)-CH_2-$ | O | $CH_2-CH_2-COOC_3H_7$ | $CH_3$ | $CH_3$ | H | oil | >90 |
| 37 | $-CH(CH_3)-CH_2-$ | O | $(CH_2)_5-COOCH_3$ | $CH_3$ | $CH_3$ | H | oil | >90 |
| 38 | $-CH_2-CH_2-$ | O | $CH_3$ | $CH_3$ | H | $CH_3$ | 128–130 | 64 |
| 39 | $-CH_2-CH_2-$ | O | $n-C_{12}H_{25}$ | $CH_3$ | H | $CH_3$ | 70–72 | 57 |

The present invention also comprises pharmaceutically acceptable bioprecursors of the new active compounds of the present invention.

For the purpose of this specification the term 'pharmaceutically acceptable biprecursor' of an active compound of the invention means a compound having a structural formula different from the active compound but which nonetheless, upon administration to a warm-blooded animal is converted in the patient's body to the active compound.

What is claimed is:

1. A pharmaceutical composition containing as an active ingredient a hypolipidemically effective amount of a compound which is an alkylurea of the formula

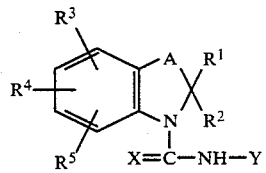

(I)

in which
X denotes oxygen or sulphur and
A represents

in which
R' and R" are identical or different and each denote a hydrogen atom or an alkyl radical with 1 to 4 carbon atoms,
Y represents R or a radical

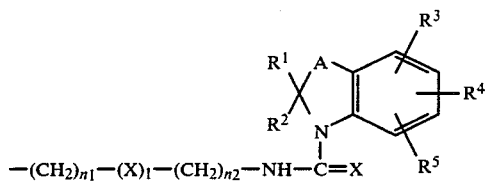

in which
$n_1$ and $n_2$ denote integers from 3 to 9 and
l denotes 0 or 1 and
in which
X and A are as defined above and in which all $R$–$R^5$ radicals are as follows:
  R represents a straight-chain, branched, cyclic, saturated or mono-unsaturated aliphatic hydrocarbon radical with 4 to 20 carbon atoms, which is optionally substituted by halogen, trifluoromethyl, hydroxyl or alkoxy or alkoxycarbonyl, with, in each case, 1 to 6 carbon atoms in the alkoxy radical, or by phenyl, the phenyl radical in turn optionally carrying 1 or 2 substituents selected from halogen, trifluoromethyl, hydroxyl, alkyl with 1 to 2 carbon atoms and alkoxy with 1 to 2 carbon atoms
  $R^1$ represents a hydrogen atom or a non-steric-hinderable $C_1$–$C_6$ alkyl radical,
  $R^2$ represents a non-steric hinderable $C_1$–$C_6$ alkyl radical and
  $R^3$, $R^4$ and $R^5$ are identical or different and each represent a hydrogen or halogen atom or a hydroxyl, cyano, $C_1$–$C_6$ alkyl, $C_1$–$C_6$ alkoxy, ($C_1$–$C_6$ alkoxy)-carbonyl, ($C_1$–$C_6$-alkyl)-carbonyl, a phenyl or phenoxy radical, optionally substituted by 1 to 2 substituents selected from halogen, trifluoromethyl, hydroxyl, $C_1$–$C_2$-alkyl or $C_1$–$C_2$-alkoxy
in admixture with an inert pharmaceutical carrier.

2. A composition according to claim 1 in which the active ingredient is a compound in which
  R represents a straight-chain, branched, cyclic saturated or unsaturated aliphatic hydrocarbon radical with 4 to 20 carbon atoms, which is optionally substituted by halogen, hydroxyl or alkoxy or alkoxycarbonyl with, in each case, 1 to 6 carbon atoms in the alkoxy radical, or by phenyl, the phenyl radical in turn optionally carrying 1 or 2 substituents selected from halogen, trifluoromethyl, hydroxyl, alkyl with 1 to 2 carbon atoms and alkoxy with 1 to 2 carbon atoms,
  $R^1$ represents a hydrogen atom or a non-steric-hinderable alkyl radical with 1 to 4 carbon atoms,
  $R^2$ represents a non-steric-hinderable alkyl radical with 1 to 4 carbon atoms,
  $R^3$, $R^4$ and $R^5$ are identical or different and each represent a hydrogen or halogen atom or a hydroxyl, cyano, trifluoromethyl, alkyl, alkylcarbonyl, alkoxy or alkoxycarbonyl radical, the above-mentioned alkyl and alkoxy radicals or moieties being non-steric-hinderable and containing 1 to 4 carbon atoms in each case, or represent a phenyl or phenoxy radical, the phenyl radical or moiety optionally being monosubstituted or disubstituted by halogen, trifluoromethyl or alkoxy with 1 to 2 carbon atoms,
  X denotes oxygen or sulphur and
  A represents

in which
R' and R" are identical or different and each denote a hydrogen atom or an alkyl radical with 1 to 4 carbon atoms, 3. A composition according to claim 1 in which the active ingredient is a compound of the formula

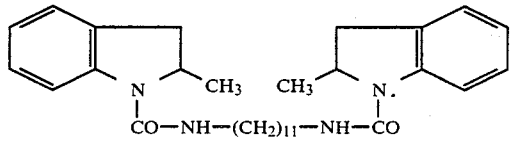

4. A pharmaceutical composition of claim 1 in the form of a sterile or physiologically isotonic aqueous solution.

5. A composition according to claim 1 containing from 0.5 to 95% of the said active ingredient, by weight.

6. A composition according to claim 1 in which Y denotes the radical R.

7. A method of combating diseases of the lipometabolism in warm-blooded animals which comprises administering to the animals a hypolipidemically effective amount of a compound as defined in claim 31 either alone, or in admixture with an inert pharmaceutical carrier in the form of a medicament.

8. A method according to claim 7 in which the active compound is administered in an amount of 5 to 100 mg per kg of body weight per day.

9. A method according to claims 7 or 8 in which the active compound is administered orally.

10. A method of combating diseases of the lipometaboolism in warm-blooded animals which comprises administering to the animals a hypolipidemically effective amount of a compound as defined in claim 31 wherein Y denotes the radical R, either alone or in admixture with an inert pharmaceutical carrier in the form of a medicament.

11. An alkylurea derivative of the formula

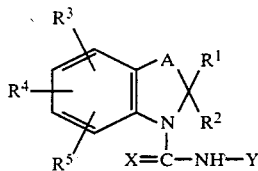
(I)

in which
Y represents R and R represents a straight-chain, branched or cyclic alkyl or alkenyl radical, with in each case 6 to 18 carbon atoms, the said alkyl and alkenyl groups optionally being substituted by chlorine, bromine, fluorine, alkoxy with 1 to 4 carbon atoms, or by phenyl, $R^1$ and $R^2$ are identical or different and each represent an alkyl radical with 1 or 2 carbon atoms, $R^3$, $R^4$ and $R^5$ are identical or different and each represent a hydrogen, chlorine, or bromine atom or a trifluoromethyl, alkyl, or alkoxy radical, the said alkyl and alkoxy radicals or moieties each containing 1 to 4 carbon atoms, or represent a phenoxy or chlorophenoxy radical, A represents

in which
R' and R" are identical or different and each denote a hydrogen atom or a methyl or ethyl radical, and X represents oxygen.

12. An alkylurea derivative according to claim 11 in which Y=R,
R represents a straight-chain, branched or cyclic alkyl or alkenyl radical with, in each case, 6 to 18 carbon atoms, which is optionally substituted by chlorine, bromine, fluorine or alkoxy with 1 to 4 carbon atoms, $R^1$ and $R^2$ are identical or different and each represent a methyl or ethyl radical, $R^3$, $R^4$ and $R^5$ are identical or different and each represent a hydrogen, chlorine or bromine atom a trifluoromethyl, phenoxy or chlorophenoxy radical or an alkyl, alkylmercapto or alkoxy radical with, in each case, 1 or 2 carbon atoms, X represents oxygen and
A represents one of the following radicals:

in which

R' and R" each denote a hydrogen atom or a methyl or ethyl radical.

13. An alkylurea derivative according to claim 12 in which R' and R" each denote a methyl or ethyl radical.

14. An alkylurea derivative of the formula

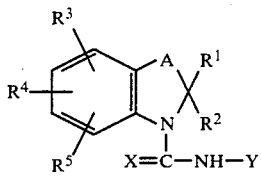
(I)

in which
Y denotes a radical

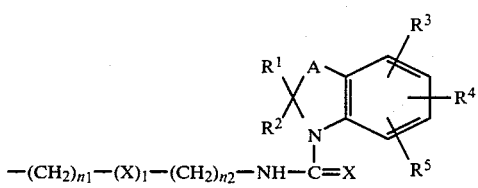

in which
$n_1$ and $n_2$ denote integers from 3 to 9 and 1 denotes 0 or 1, in which
$R^1$ and $R^2$ are identical or different and each represent an alkyl radical with 1 or 2 carbon atoms, $R^3$, $R^4$ and $R^5$ are identical or different and each represent a hydrogen, chlorine, or bromine atom or a trifluoromethyl, alkyl, alkylmercapto, or alkoxy radical, the said alkyl and alkoxy radicals or moieties each containing 1 to 4 carbon atoms, or represent a phenoxy or chlorophenoxy radical, A represents

in which
R' and R" are identical or different and each denote a hydrogen atom or a methyl or ethyl radical, and
X represents oxygen.

15. A compound of claim 11 which is

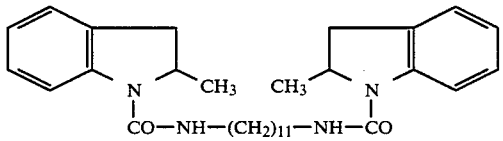

* * * * *

UNITED STATES PATENT AND TRADEMARK OFFICE
CERTIFICATE OF CORRECTION

PATENT NO. : 4,510,156

DATED : April 9, 1985

INVENTOR(S) : Kabbe et al.

It is certified that error appears in the above-identified patent and that said Letters Patent is hereby corrected as shown below:

Col. 16, lines 50 and 63    Delete "claim 31" and substitute --claim 1--

Col. 18, line 51    Delete "claim 11" and substitute --claim 14--

Signed and Sealed this

Twenty-fourth Day of December 1985

[SEAL]

Attest:

DONALD J. QUIGG

Attesting Officer    Commissioner of Patents and Trademarks